US011534070B2

United States Patent
Tsutsumi et al.

(10) Patent No.: US 11,534,070 B2
(45) Date of Patent: Dec. 27, 2022

(54) BLOOD PRESSURE MEASUREMENT DEVICE WITH SOUND DETECTION FUNCTION AND BLOOD PRESSURE MEASUREMENT METHOD

(71) Applicants: OMRON CORPORATION, Kyoto (JP); OMRON HEALTHCARE CO., LTD., Kyoto (JP)

(72) Inventors: Masakazu Tsutsumi, Kyoto (JP); Shingo Yamashita, Kyoto (JP)

(73) Assignees: OMRON CORPORATION, Kyoto (JP); OMRON HEALTHCARE CO., LTD., Kyoto (JP)

( * ) Notice: Subject to any disclaimer, the term of this patent is extended or adjusted under 35 U.S.C. 154(b) by 575 days.

(21) Appl. No.: 16/544,995

(22) Filed: Aug. 20, 2019

(65) Prior Publication Data

US 2019/0365245 A1 Dec. 5, 2019

Related U.S. Application Data

(63) Continuation of application No. PCT/JP2018/009570, filed on Mar. 12, 2018.

(30) Foreign Application Priority Data

Mar. 15, 2017 (JP) .............................. JP2017-050247

(51) Int. Cl.
*A61B 5/0205* (2006.01)
*A61B 5/00* (2006.01)
*A61B 5/022* (2006.01)

(52) U.S. Cl.
CPC .......... *A61B 5/0205* (2013.01); *A61B 5/4806* (2013.01); *A61B 5/022* (2013.01); *A61B 2562/0204* (2013.01)

(58) Field of Classification Search
CPC ..... A61B 5/0205; A61B 5/4806; A61B 5/022; A61B 2562/0204; A61B 5/021;
(Continued)

(56) References Cited

U.S. PATENT DOCUMENTS

2005/0187480 A1  8/2005  Kario et al.
2007/0118054 A1  5/2007  Pinhas et al.
(Continued)

FOREIGN PATENT DOCUMENTS

CN     1903117    1/2007
CN     103108592  5/2013
(Continued)

OTHER PUBLICATIONS

International Preliminary Report on Patentability dated Sep. 19, 2019 in International (PCT) Application No. PCT/JP2018/009570.
(Continued)

*Primary Examiner* — David J. McCrosky
*Assistant Examiner* — Clarissa Cuevas
(74) *Attorney, Agent, or Firm* — Wenderoth, Lind & Ponack, L.L.P.

(57) ABSTRACT

A blood pressure measurement device measures a blood pressure of a subject by a blood pressure measurement unit, detects a body sound of the subject during blood pressure measurement by a sound detection unit. The measured blood pressure and the detected body sound are recorded in association with each other by time information. The factor for the increase of measured blood pressure value can be specified by showing the chronological blood pressure measurement result along with checking the presence or absence of a body sound such as snoring etc.

4 Claims, 6 Drawing Sheets

(58) Field of Classification Search
CPC ............ A61B 5/02208; A61B 5/02216; A61B 5/02225; A61B 5/0225; A61B 5/0823; A61B 5/0826; A61B 7/003; A61B 5/02108; A61B 5/02116; A61B 5/02125; A61B 5/02133; A61B 5/02141; A61B 5/02233; A61B 5/02241; A61B 5/02255; A61B 5/023; A61B 5/0235; A61B 5/024; A61B 5/02405; A61B 5/02411; A61B 5/02416; A61B 5/02422; A61B 5/02427; A61B 5/02433; A61B 5/02438; A61B 5/02444; A61B 5/0245; A61B 5/02455; A61B 5/025; A61B 5/0255; A61B 5/026; A61B 5/0261; A61B 5/0263; A61B 5/0265; A61B 5/027; A61B 5/0275; A61B 5/02755; A61B 5/028; A61B 5/0285; A61B 5/029; A61B 5/0295; A61B 7/00; A61B 7/02; A61B 7/023; A61B 7/026; A61B 7/04; A61B 7/045
See application file for complete search history.

(56) References Cited

U.S. PATENT DOCUMENTS

| | | | |
|---|---|---|---|
| 2013/0066166 A1* | 3/2013 | Burnett | A61B 5/16 600/301 |
| 2013/0158363 A1 | 6/2013 | Zoghbi | |
| 2013/0245502 A1 | 9/2013 | Lange et al. | |
| 2016/0029965 A1* | 2/2016 | Simon | A61B 5/369 600/301 |
| 2017/0095669 A1* | 4/2017 | Libbus | A61N 1/36139 |
| 2018/0228434 A1* | 8/2018 | Dwarika | A61B 5/08 |
| 2022/0008746 A1* | 1/2022 | Malchano | A61N 1/36092 |

FOREIGN PATENT DOCUMENTS

| | | | |
|---|---|---|---|
| CN | 203263375 | | 11/2013 |
| CN | 105411305 | | 3/2016 |
| JP | 2005-34470 | | 2/2005 |
| JP | 2005-237472 | | 9/2005 |
| JP | 2008-206553 | | 9/2008 |
| JP | 2009-532072 | | 9/2009 |
| JP | 2010158289 A | * | 7/2010 |
| JP | 2012-030577 | | 2/2012 |
| WO | 2012/018029 | | 2/2012 |

OTHER PUBLICATIONS

Decision to Grant a Patent dated Mar. 2, 2021 in corresponding Japanese Patent Application No. 2017-050247 with English translation.
Office Action dated Jul. 14, 2021 in Chinese Patent Application No. 201880013845.0, with English-language translation.
Office Action dated Jan. 10, 2022 in corresponding Chinese Patent Application No. 201880013845.0 with English language translation.
Office Action dated May 7, 2022 in corresponding Chinese Application No. 201880013845.0 with English translation.
International Search Report dated May 1, 2018 in International (PCT) Application No. PCT/JP2018/009570 with English translation.

* cited by examiner

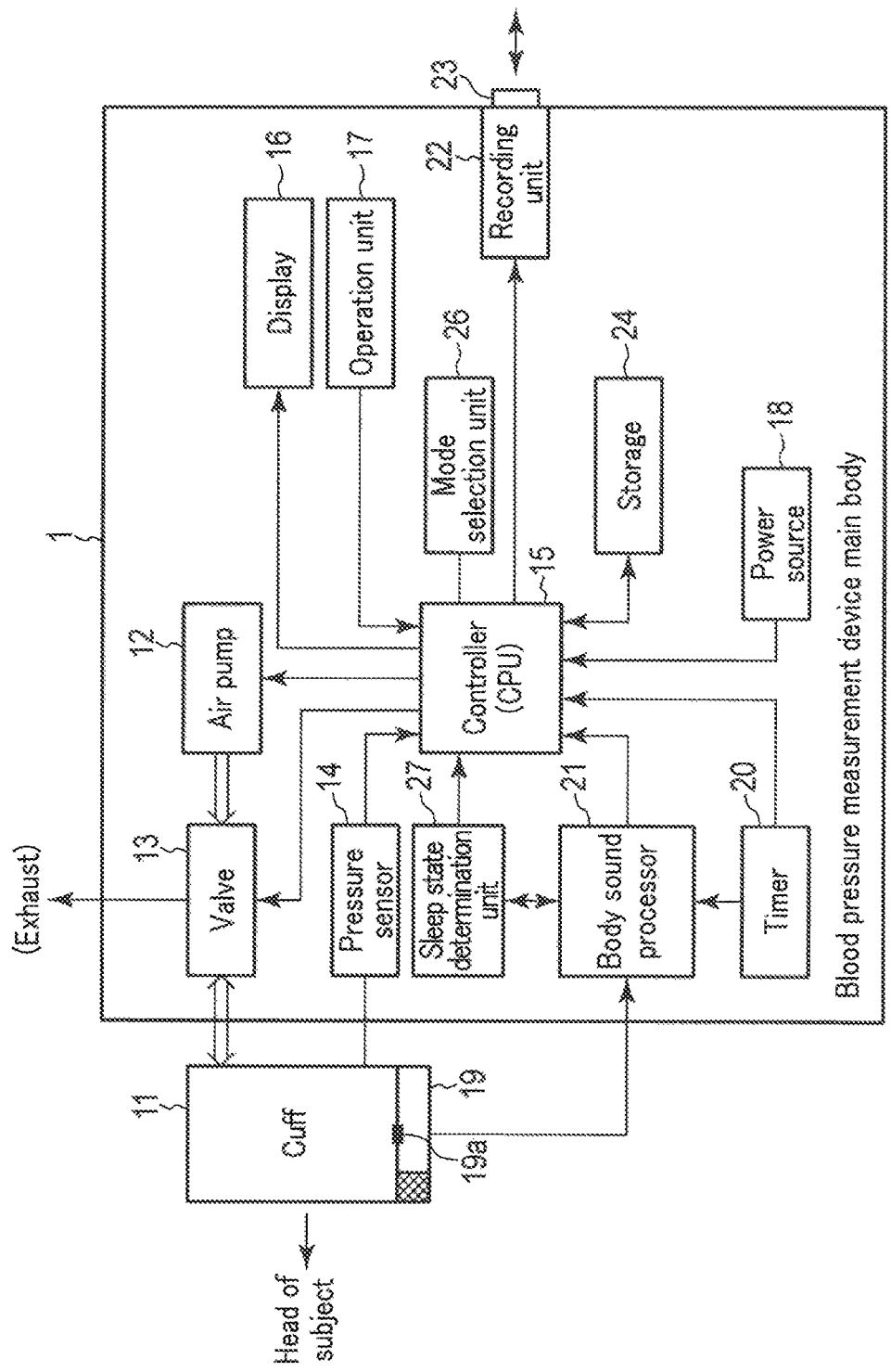
F I G. 1

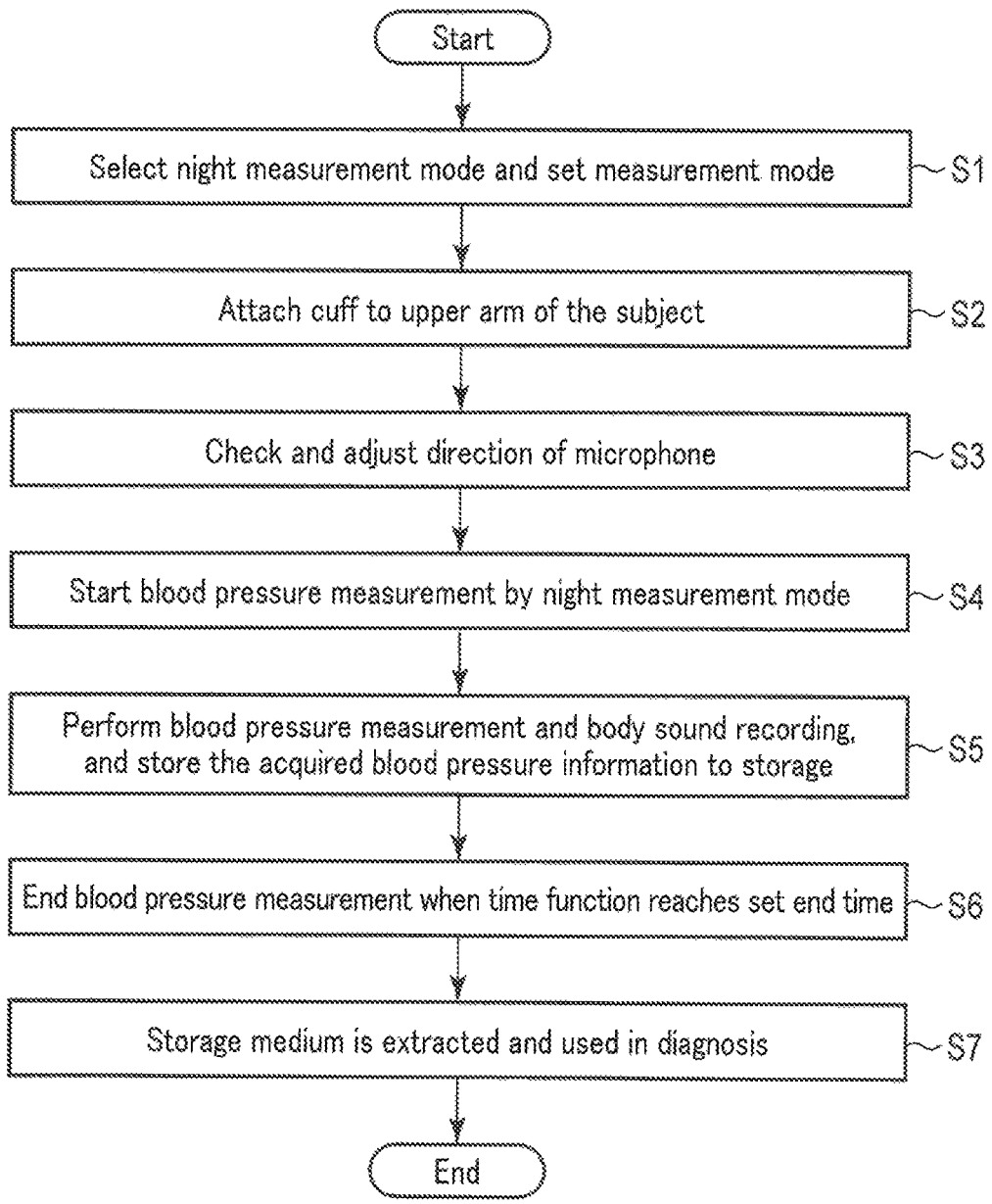
F I G. 5

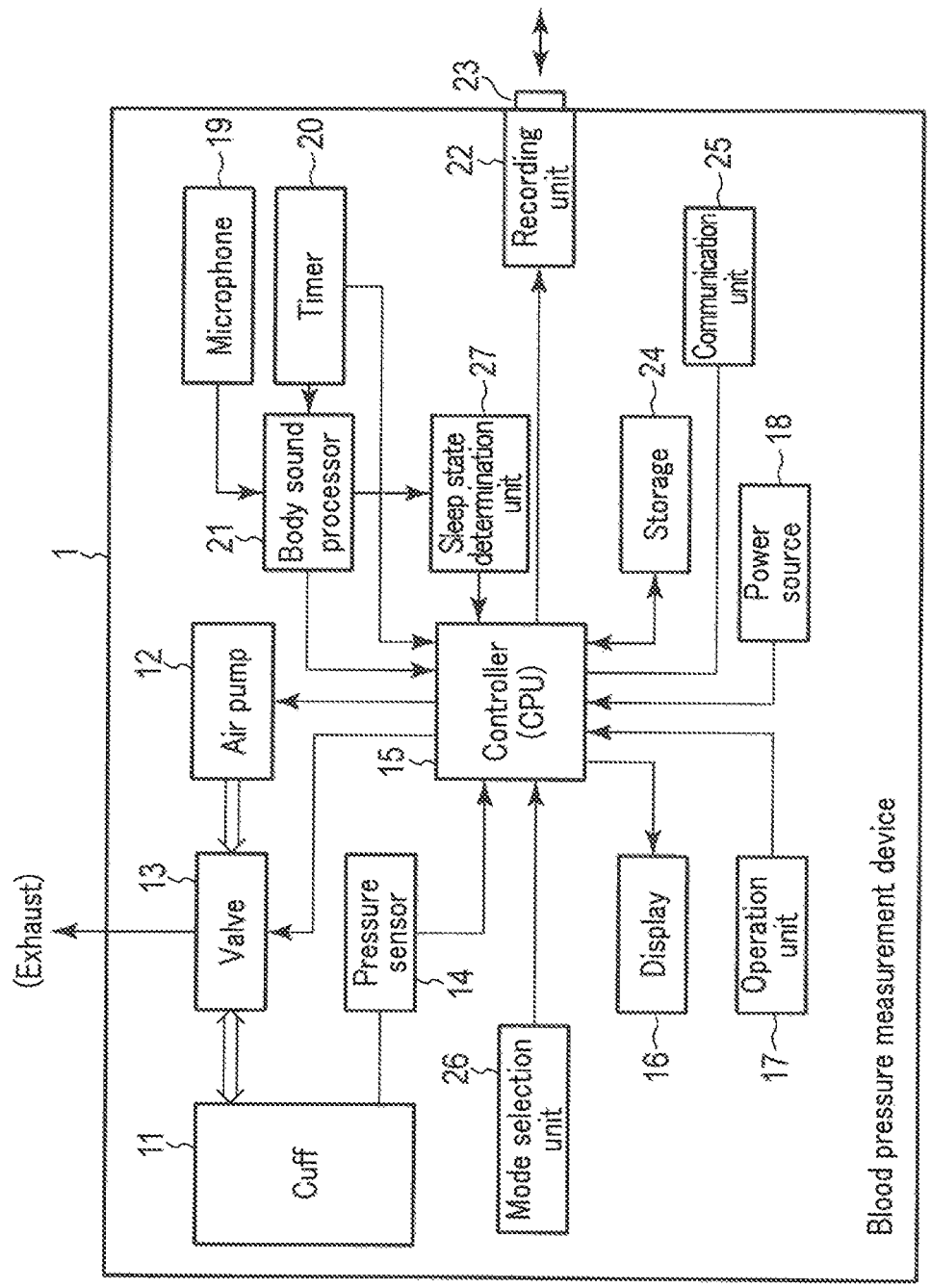
F I G. 6

ID AND BLOOD PRESSURE
BLOOD PRESSURE MEASUREMENT DEVICE WITH SOUND DETECTION FUNCTION AND BLOOD PRESSURE MEASUREMENT METHOD

CROSS-REFERENCE TO RELATED APPLICATIONS

This is a Continuation Application of PCT Application No. PCT/JP2018/009570, filed Mar. 12, 2018, and based upon and claims the benefit of priority from the Japanese Patent Application No. 2017-050247, filed Mar. 15, 2017, the entire contents of all of which are incorporated herein by reference.

FIELD

The present invention relates generally to a blood pressure measurement device with a sound detection function and a blood pressure measurement method for measuring blood pressure together with detecting a body sound emitted by a subject.

BACKGROUND

Conventionally, physical information used in diagnosis is obtained using various measurement devices. For example, blood pressure is measured by wrapping a blood pressure measurement device around an upper arm of the subject. Further, a miniaturized wrist-type blood pressure measurement device for attaching to the wrist (forearm) is also used.

There is increased interest in obstructive sleep apnea (OSP) and blood pressure measurement during sleep performed. For example, a blood pressure meter capable of measuring for 24 hours including sleep hours is proposed (refer to International Publication No. WO 2012-18029A1).

SUMMARY

A blood pressure measurement device with a sound detection function according to the First aspect includes a blood pressure measurement unit for measuring a blood pressure of a subject, a sound detection unit for detecting a body sound of the subject during blood pressure measurement by the blood pressure measurement unit, and a recording unit configured to record the blood pressure measured by the blood pressure measurement unit and the body sound detected by the sound detection unit in association with each other by time information.

The sound detection unit of the blood pressure measurement device with a sound detection function according to the Second aspect includes a microphone configured to detect sounds, and the microphone is configured to detect the body sound including at least one of snoring, coughing, sneezing, hiccups, sleep talking and teeth grinding from a mouth of the subject, and affects a blood pressure value to be measured.

The blood pressure measurement unit of the blood pressure measurement device with a sound detection function according to the Third aspect includes a cuff configured to be attached to the subject, and the microphone is configured to be rotatably attached to the cuff via a rotation adjustment mechanism.

The blood pressure measurement unit of the blood pressure measurement device with a sound detection function according to the Fourth aspect includes a blood pressure measurement mode for performing a plurality of blood pressure measurements at time intervals, and is configured to start recording the body sound by the microphone before a start of each of the blood pressure measurements when measuring the blood pressure in the blood pressure measurement mode.

The blood pressure measurement device with a sound detection function according to the Fifth aspect further includes a cuff integral with the blood pressure measurement device, and the microphone is provided on the blood pressure measurement device or the integrally-configured cuff so as to be directed to the mouth of the subject when the blood pressure measurement device is attached to an upper arm of the subject.

A blood pressure measurement method using a sound detection function according to the Sixth aspect includes a blood pressure measurement step for measuring a blood pressure of a subject, a sound detection step for detecting a body sound of the subject during blood pressure measurement, and a recording step for recording the body sound detected in the sound detection step and the blood pressure measured in the blood pressure measurement step in association with each other by time.

According to the First and Sixth aspects, the factor for the increase of measured blood pressure value can be specified by showing the chronological blood pressure measurement result along with checking the presence or absence of snoring etc. To confirm other body sounds generated during the blood pressure measurement can be one basis for determination of diagnosis, as well.

According to the Second aspect, the factor for the increase of the measured blood pressure value can be specified by checking the recorded body sound such as snoring or the like.

According to the Third aspect, the directivity of the microphone can be adjusted towards the mouth of the subject.

According to the Fourth aspect, power consumption can be reduced since a plurality of blood pressure measurements are performed at given intervals during sleep, and blood pressure measurements can be performed over a long period of time. Further, it is possible to perform consecutive blood pressure, measurements.

According to the Fifth aspect that adopts a cuff integrated upper arm blood pressure measurement device, there is no cable or tube connecting the cuff and blood pressure measurement device main body, thus, there is no restriction on body movement such as the subject turning over during sleep, and no need to worry about the directivity of the microphone from deviating due to the cuff deviating from the measuring point of the upper arm during sleep.

According to the Sixth aspect, the factor for the increase of the measured blood pressure value can be specified by showing a chronological blood pressure measurement result along with checking the presence or absence of snoring or the like. To confirm other body sounds generated during the blood pressure measurement can be one basis for determination of diagnosis, as well.

BRIEF DESCRIPTION OF TEE DRAWINGS

FIG. 1 is a block diagram indicating a configuration example of an upper arm type blood pressure measurement device provided with a sound detection unit according to the First embodiment.

FIG. 5 is a flowchart for explaining a blood pressure measurement process.

FIG. 6 is a block diagram indicating a configuration example of a wrist type blood pressure measurement device provided with a sound detection unit according to the Second embodiment.

DETAILED DESCRIPTION

The blood pressure value measured during sleep by the aforementioned blood pressure measurement device capable of measuring for long periods of time may be affected in its precision since there is a tendency for such a measured value to be higher than the actual blood pressure value if the subject snores or coughs during the measurements.

Further, even if the measured blood pressure value shows abnormality, proper determination of whether such abnormality is a result of diseases etc. of the subject or is the result of snoring or coughs cannot be made unless the person who performs the diagnosis or the measurer is present at that time.

The purpose of one embodiment is to provide a blood pressure measurement device with a sound detection function and a blood pressure measurement method that allow for recording blood pressure information measured during a blood pressure measurement period and body sounds emitted by the sleeping subject during the blood pressure measurement period in tempo-al association with each other.

In the following, embodiments of the present invention will be described in detail with reference to the figures.

First Embodiment

Figure 2:
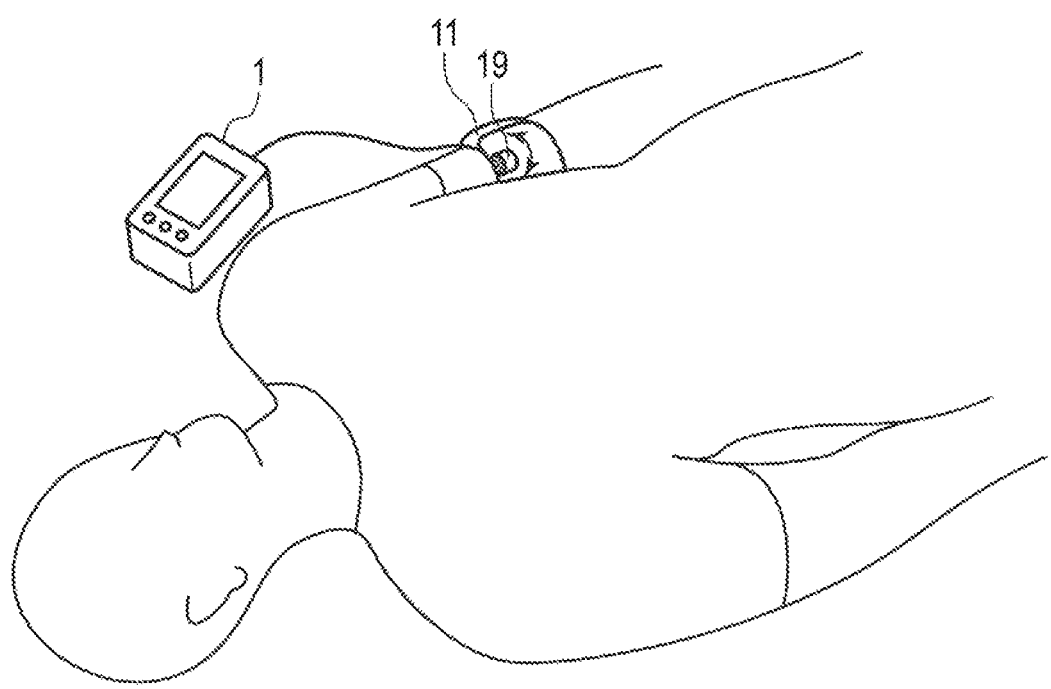
FIG. 2 is a diagram indicating a position of a microphone when a cuff is attached to the subject.

The following explains the blood pressure measurement device with a sound detection function according to the First embodiment of the present invention, FIG. 1 is a block diagram indicating a configuration example of the upper arm type blood pressure measurement device provided with the sound detection unit according to the First embodiment. FIG. 2 is a diagram indicating a position of a microphone when the cuff is attached to the subject.

The upper arm type blood pressure measurement device (blood pressure measurement device) 1 of the present embodiment configures a blood pressure measurement unit by including a cuff 11 for applying pressure to blood vessels of the subject, an air pump 12 for supplying gas (air), a valve 13 for feeding air from the air pump 12 to the cuff 11 and discharging air from the cuff 11 to the exterior, a pressure sensor 14 for measuring the internal pressure of the cuff and the blood pressure and a controller (CPU) 15 for controlling the entire device to perform blood pressure measurements.

Further, the blood pressure measurement device 1 includes a display 16 for displaying detected blood pressure information or operation matters etc., an operation unit 17 including operation buttons or touch panels etc. for measurement setting and various inputs, a power source 18 including rechargeable batteries or primary batteries etc., a storage 24 for storing blood pressure information associated with time information, and a communication unit 25 for communicating with an external device (not shown) and outputting blood pressure information. In addition, the blood pressure measurement device 1 includes a microphone 19 having directivity which is the sound detection unit, a timer 20 for temporally associating the hereinafter described blood pressure information with sound information, a sound processor 21 for processing a sound signal produced by the microphone 19, a small storage medium 23 such as a detachable SD memory card etc., a recording unit 22 for recording blood pressure information etc, to the storage medium 23, a mode selection unit 26 for selecting one of a preset plurality of measurement modes or selecting a measurement interval or a measurement time to set a measurement mode, and a sleep state determination unit 27 for determining a sleep state of the subject. The blood pressure measurement technique, as well as the configuration etc, of the air pump 12, valve 13, pressure sensor 14 and cuff 11 of the present embodiment are publically known. The timer 20 may utilize the clock function included by the blood pressure measurement device 1.

The measurement modes that can be selected with the mode selection unit 26 of the blood pressure measurement device 1 include a continuous measurement mode that continuously measures between starting operation and stopping operation, a time setting mode for a measurer such as a nurse or the like or the subject to set the measurement time, and a night measurement mode for measuring multiple times at any set time intervals during sleep. This night measurement mode can reduce the power consumption of the power source and allows for measurements over long periods, of time.

The timer 20 includes the clock function and a time stamp function to set the measurement timings and associate the period or the time with the measured blood pressure information.

The microphone 19 is preferably small and light and of a unidirectional configuration of only picking up sounds in one direction without picking up surrounding sounds. The microphone 19 is arranged on the outer surface side of the cuff 11 and attached so that it can be rotated in a horizontal direction (direction parallel to the surface of the cuff) by a rotation adjustment mechanism 19a. As shown in FIG. 2, the directivity of the microphone 19 can be adjusted towards the mouth of the subject by the rotation adjustment mechanism 19a when the cuff 11 is attached to the upper arm of the subject.

The microphone 19 of the present embodiment detects a body sound of the subject, and the body sound is at least one of snoring, coughing, sneezing, hiccups, sleep talking and teeth grinding etc. which is produced from the mouth and not beating sounds or pulse sounds; and specifically, it is important that they are sounds that affect blood pressure values during blood pressure measurements.

A sound processor 21 performs filter processing or the like so as to extract the above-mentioned body sounds from the sound signals generated by the microphone 19, which means to perform sound processing to remove sounds generated in the cloth or surrounding environment inputted to the microphone 19, in other words, external noise. Further, overlapping snoring that has an obviously different sound level or repeats at a different interval will be determined as another person's snoring and will be handled in the same manner as noise. The doctor can understand the factor for the blood pressure change and easily decide on the treatment policy since the sound generation source is specified when analyzing the measured blood pressure value data.

Further, the time information outputted from the timer 20 is associated when performing body sound processing. The controller 15 associates the measured blood pressure value and the body sound with time information by the timer 20 and sequentially stores them to a storage 24 for each measurement.

The recording unit 22 records the blood pressure information read from the storage 24 to a storage medium 23 which is for example a rewritable small non-volatile storage medium such as a micro SD memory card, etc. The storage medium 23 is inserted into a slot of a computer which is the exterior equipment, so that the blood pressure information is read and is used in diagnosis made by the doctor. Further, the blood pressure information can be transmitted by a communication using a wireless LAN network etc. by the hereinafter described communication unit 25.

The communication unit 25 may transmit/receive information with the exterior equipment by wireless communication. As a communication method, for example, radio wave reception intensity method (RSSI: Received Signal Strength Indicator) used in PHS or Bluetooth (Trademark Registered), Cell-ID method, GPS method or CDMA method, radio wave arrival, time difference method (TDOA: Time Difference of Arrival) used in Wi-Fi terminals can be used. Further, other than wireless means, methods such as optical communication and wired communication are also possible.

The sleep state determination unit 27 may use a publicly-known sleep meter, and for example, determines whether the subject is in the sleep state and is in deep sleep (non-REM sleep) or not from the movement of the body of the subject using an acceleration sensor or the like. If the microphone 19 is used and if the sound picked up by the microphone 19 is snoring, it can be determined that the subject is in the sleep state. In addition, it is also possible to measure the heart rate to determine whether the subject is in the sleep state or not.

Figure 3:
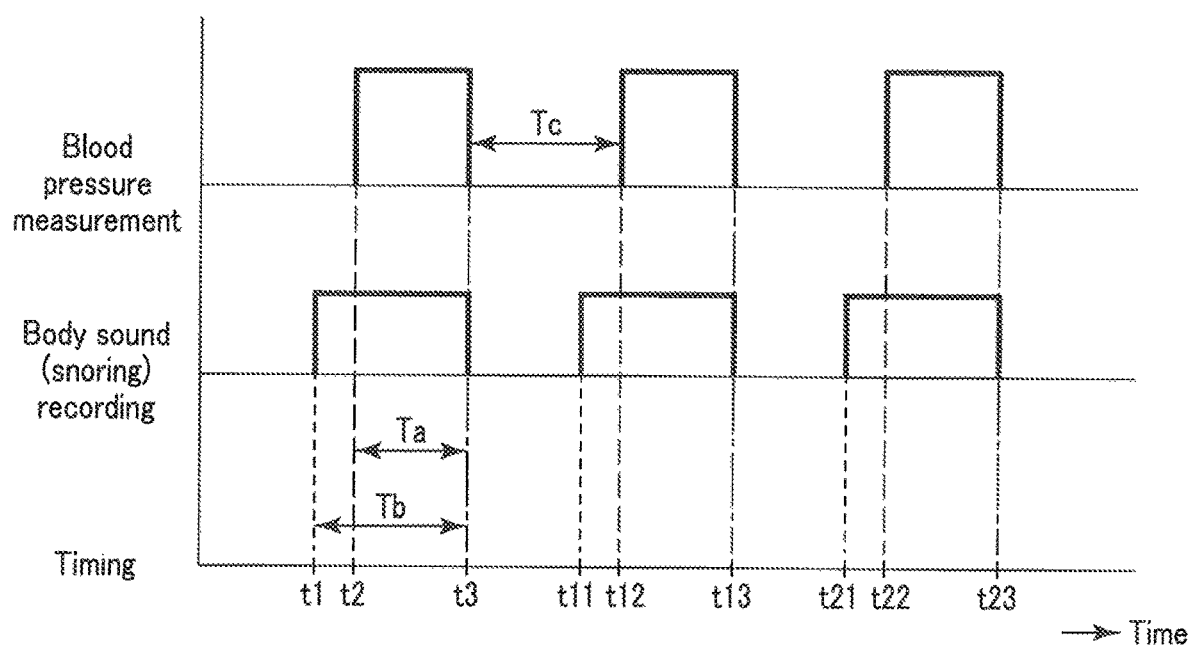
FIG. 3 is a diagram indicating a timing of blood pressure measurement and body sound recording in a night measurement mode.

The timing of blood pressure measurement and timing of a body sound recording is explained by referring to FIG. 3.

The recording of a body sound in the present embodiment is performed during a sleep state of the subject, FIG. 3 indicates a timing of blood pressure measurement and body sound recording under the night measurement mode.

This night measurement mode performs a plurality of blood pressure measurements by repeating the blood pressure measurement for a predetermined measurement period Ta at regular intervals Tc. Although continuous blood pressure measurement is possible, it is possible to reduce the power consumption of the battery which is a power source S and to enable blood pressure measurement over long periods of time under the night measurement mode with respect to the continuous blood pressure measurement. As mentioned, the blood pressure measurement for the blood pressure measurement period Ta is repeated at the time intervals Tc.

The body sound recording does not need to be continuous since importance is placed on whether a body sound is generated during a blood pressure measurement or not, and therefore, a recording, period Tb of the body sound recording can be set in connection with the blood pressure measurement period Ta. According to the present embodiment, as shown in FIG. 3, a recording start time t1 is set a few minutes before a start time t2 of the blood pressure measurement period.

More specifically, the night measurement mode assumes the selection of a further two measurement modes, namely, setting a measurement time interval and setting measurement times. In other words, it is possible to control the measurement to be performed at set intervals or at specific times such as 21:00, 22:00, etc. For the setting of the measurement interval, one of 10-minute, 15-minute, 30-minute or 1-hour intervals, or any combination thereof can be selected. Further, for the setting of times, the measurement time can be set to every 30 minutes, 1 hour . . . ; for example, if the measurement time is every hour, the times may be set as 21:00 as a start time, and 22:00, . . . 5:00 and 6:00 as an end time. For example, in FIG. 4, the measurement time is set to every 30 minutes. Further, the blood pressure measurement period is selected from the range of 5 minutes, 10 minutes and 15 minutes. Here, the recording time of the body sound is for example, set 5 minutes before a period of the blood pressure measurement, and the recording period of the body sound is for example, set 5 minutes longer such as 15 minutes, 20 minutes etc. than a period of the blood pressure measurement. Naturally, this is not limited to 5 minutes, etc., and can be suitably set depending on the ambient temperature or the condition of the subject.

Such setting allows to specify the generation source, strength and rhythm of the sound by starting the recording of the body sound a little before the blood pressure measurement. Further, a recording end time t3 can be the same as the blood pressure measurement end time. By intermittently performing body sound recording, the data processing amount in the controller 15 can be reduced and the data amount to be stored in the storage 24 can be reduced.

In this example, the recoding time of the body sound is defined by the setting time, so the blood pressure measurement and body sound recording are both performed regardless of the presence or absence of generation of the body sound. In this relation, the so-called retroactive recording technique is known, in which held data is subjected to recording retroactively from the sound generation time in response to recognizing a sound occurrence. By combining this retroactive recording and the aforementioned intermittent body sound recording periods, the data amount to be stored can be reduced since the information of the blood pressure measurement period without a generation of the body sound can be omitted.

Here, the blood pressure value and snoring level will be explained in light of FIG. 4.

Figure 4:
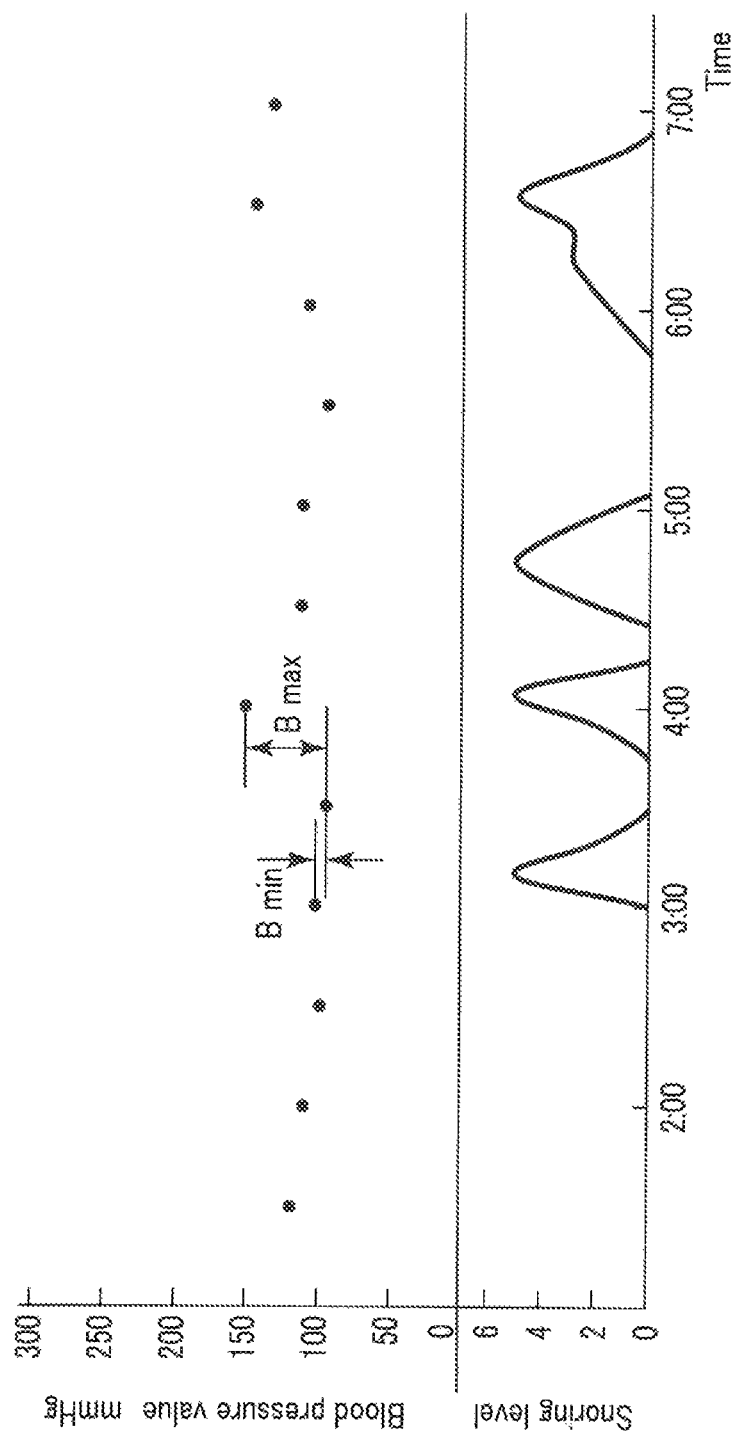
FIG. 4 is a diagram indicating a snoring level for a measured blood pressure value.

As shown in FIG. 4, a difference of approximately 20 to 60 (mmHg) is involved between the minimum (hmin) and maximum (hmax) blood pressure values depending on when there is snoring and when there is no snoring. Generally, it is known that there is a tendency for the blood pressure value to increase when generating body sounds such as snoring.

Therefore, when the blood pressure measurement result shown in FIG. 4 is used, the reason for the rise of the blood pressure value can be specified by checking for the presence or absence of snoring at the part indicating a specifically high blood pressure value. Confirmation of other body sounds generated during the blood pressure measurement can be a basis for determination of diagnosis, as well. Thus, the strength of the influence of the body sound can be confirmed and can be used in treatment.

Next by referring to a flowchart shown in FIG. 5, the process of the blood pressure measurement will be explained.

The night measurement mode is selected by the mode selection unit 26 of the blood pressure measurement device 1, and selecting and setting the aforementioned further measurement mode are performed (step S1).

Next, the cuff 11 is attached to an upper arm of the subject before bedtime (step S2) and a position of the microphone 19 is checked. As shown in FIG. 2, the rotation adjustment mechanism 19a is adjusted so that the directivity of the microphone 19 is adjusted towards the mouth of the subject (step S3).

The blood pressure measurement in the night measurement mode starts when the subject goes to sleep (step S4). This blood pressure measurement can start when the subject goes to sleep or can start by using the aforementioned sleep state determination unit 27.

A periodic blood pressure measurement and body sound recording in the night measurement mode are performed, and the acquired blood pressure information and body sound information are sequentially stored to the storage 24 in association with the time information by the timer 20 (step S5).

When the end time set by the measurer or the subject reaches, for example, 7:00 in the morning, the blood pressure measurement ends (step S6) With the end of the measurement, all of the blood pressure information stored at any time in the storage 24 is transferred to the recording unit 22 to be stored in the storage medium 23 (step S7).

The storage medium 23 is extracted by a nurse, etc. and is handed over to the doctor to be utilized for diagnosis.

The description has assumed the configuration example where the upper arm blood pressure measurement device in the embodiment is constituted by the cuff 11 and the blood pressure measurement device main body 1 which are separate and connected by a cable etc.; however, the cuff 11 and the blood pressure measurement device main body 1 may be integrated, similarly to the hereinafter described wrist type blood, pressure measurement device. The sound detection unit configured with the aforementioned microphone 19, sound processor 21 and recording unit 22, and other configurations can be arranged in the main body of the cuff integrated upper arm type blood pressure measurement device. The microphone 19 can be provided on either the blood pressure measurement device main body 1 side or the cuff 11 side since it is of an integral structure. The microphone 19 in this case is arranged so that the directivity will be towards the mouth of the subject when the blood pressure measurement device is attached to the upper arm in a similar manner to the aforementioned cuff 11.

According to the cuff integrated upper arm blood pressure measurement device, there is no cable or tube connecting the cuff 11 and blood pressure measurement device main body 1, thus, there is no restriction on body movement such as the subject turning over during sleep, and no need to worry about the directivity of the microphone 19 from deviating due to the cuff 11 deviating from the measuring point of the upper arm during sleep.

As can be seen from the above, in the present embodiment, the factor for the increase of the measured blood pressure value can be specified by showing the chronological blood pressure measurement result along with checking the presence or absence of snoring etc. To confirm other body sounds generated during the blood pressure measurement can be one basis for determination of diagnosis, as well. The power consumption can be reduced since a plurality of blood pressure measurements are performed at any intervals during sleep, and blood pressure measurements can be performed over a long period of time. However, the present embodiment is not limited to intermittent blood pressure measurements and it is possible to perform continuous blood pressure measurement.

The generation source, intensity and rhythm of sound can be specified more easily by starting the body sound recording of snoring etc. a little before the start of the blood pressure measurement. By setting the body sound recording to intermittent recording times in accordance with the blood pressure measurements, the data amount to be processed in the controller 15 can be reduced and the data amount to be stored in the storage 24 can also be reduced.

Second Embodiment

The following explains the blood pressure measurement device with sound detection function according to the Second Embodiment of the present invention by referring to FIG. 6. The aforementioned first embodiment includes an example of providing the sound detection unit for the upper arm type blood pressure measurement device, and the present embodiment is an example of providing the sound detection unit for the wrist type blood pressure measurement device for attaching to the wrist. The configurations of the present embodiment shown in FIG. 6, which are similar to the corresponding configurations shown in FIG. 1, will be referred to using the same reference numerals and a detailed explanation will be omitted.

The wrist type blood pressure measurement device (blood pressure measurement device) 1 of the present embodiment has a configuration where the components excluding the cuff 11 are stored in one case. The microphone 19 is arranged in the case and should be provided on the side facing the mouth of the subject when the case is attached to the wrist. More specifically, if the case is of a rectangular box shape, it is preferable that the microphone 19 is arranged in the side surface (first side surface) facing the shoulder or the upper end of the side surface when the forearm is extended to the foot side in the sleeping state. The first side surface corresponds to the surface of the cuff 11 to which the microphone 19 is attached as shown in FIG. 2. Further, if the forearm is bent and placed on the stomach in the sleeping state, it is preferable that the microphone 19 is arranged in the side surface of the case that faces the hip with the forearm extended and the back of the hand turned up. Therefore, in the wrist type blood pressure measurement device, the two side surfaces connected at one end are suitable for recording. Thus, the directivity of the microphone 19 is set wider compared to the first embodiment. Note that the location of the microphone 19 is not limited to inside the case, and similarly to the first embodiment, the microphone 19 may be attached to the rotation adjustment mechanism 19a provided on the cuff 11 so that the angle of the microphone 19 can be adjusted.

According to the present embodiment, in addition to the effects of the aforementioned first embodiment, a compact and lightweight configuration can be achieved since the sound detection function is provided in the wrist type blood pressure measurement device. Further, attaching to the wrist is easier than attaching to the upper arm. The function comprised by the wrist type blood pressure measurement device, such as a sleep meter can be used as the sleep state determination unit 27. By combining the sleep state information with blood pressure values and generation of the body sounds, it is easier to associate the depth of sleep and body sounds such as snoring etc, with blood pressure.

The present invention is not limited to the above described embodiments, and can be modified in practice, without departing from the gist of the invention. Moreover, the embodiments can be suitably combined; in that case, the combined advantages are obtained. Furthermore, the above-described embodiments cover various inventions, which can be extracted by combining the selected structural elements disclosed herein. For example, if the intended object and advantages are realized after some of the structural elements disclosed in the embodiments are deleted, the structure made up of the resultant structural elements may serve as an invention.

The invention claimed is:

1. A blood pressure measurement device with a sound detection function, the blood pressure measuring device comprising:
   a blood pressure measurement unit configured to measure a blood pressure of a subject;
   a sound detection unit configured to detect a body sound of the subject during blood pressure measurement by the blood pressure measurement unit; and
   processing circuitry coupled to a memory, the processing circuitry configured to record the blood pressure measured by the blood pressure measurement unit and the body sound detected by the sound detection unit in association with each other by time information, wherein
   the sound detection unit includes a microphone configured to detect sounds,
   the body sound includes at least one of snoring, coughing, sneezing, hiccups, sleep talking or teeth grinding from a mouth of the subject, the body sound affecting a blood pressure value to be measured, and
   the blood pressure measurement unit is configured to determine a start time for recording the body sound by the microphone using a timing of blood pressure measurement so as to start recording the body sound by the microphone before a start of each of a plurality of blood pressure measurements when measuring the blood pressure in a blood pressure measurement mode.

2. The blood pressure measurement device with a sound detection function according to claim 1, wherein the blood pressure measurement unit includes a cuff configured to be attached to the subject, and
   the microphone is configured to be rotatably attached to the cuff via a rotation adjustment mechanism.

3. The blood pressure measurement device with a sound detection function according to claim 1, further comprising:
   a cuff integral with the blood pressure measurement device,
   wherein the microphone is provided on the blood pressure measurement device or the cuff so as to be directed to the mouth of the subject when the blood pressure measurement device is attached to an upper arm of the subject.

4. A blood pressure measurement method using a sound detection function, the blood pressure measurement method comprising:
   measuring a blood pressure of a subject;
   detecting a body sound of the subject, the body sound including at least one of snoring, coughing, sneezing, hiccups, sleep talking or teeth grinding from a mouth of the subject, and affecting a blood pressure value to be measured, the detecting of the body sound being started before a start of the measuring of the blood pressure;
   recording the body sound detected in the detecting of the body sound and the blood pressure measured in the measuring of the blood pressure in association with each other by time information; and
   determining a start time for the recording of the body sound using a timing of blood pressure measurement so as to start the recording of the body sound before a start of each of a plurality of blood pressure measurements when performing the measuring of the blood pressure in a blood pressure measurement mode.

* * * * *